(12) United States Patent
Schmieke et al.

(10) Patent No.: US 11,517,759 B2
(45) Date of Patent: Dec. 6, 2022

(54) DEVICE FOR GENERATING ELECTRICAL, MAGNETIC AND/OR ELECTROMAGNETIC SIGNALS FOR TREATING THE HUMAN BODY, AND METHOD FOR OPERATING SUCH A DEVICE

(71) Applicant: HEALY INTERNATIONAL AG, Kränzlin (DE)

(72) Inventors: Marcus Schmieke, Kränzlin (DE); Andreas Hilburg, Oberhausen (DE); Matthias Krzizan, Nemsdorf-Göhrendorf (DE)

(73) Assignee: HEALY INTERNATIONAL AG, Kranzlin (DE)

( * ) Notice: Subject to any disclaimer, the term of this patent is extended or adjusted under 35 U.S.C. 154(b) by 102 days.

(21) Appl. No.: 16/623,156

(22) PCT Filed: Jun. 11, 2018

(86) PCT No.: PCT/EP2018/065337
§ 371 (c)(1),
(2) Date: Dec. 16, 2019

(87) PCT Pub. No.: WO2018/228987
PCT Pub. Date: Dec. 20, 2018

(65) Prior Publication Data
US 2021/0138256 A1     May 13, 2021

(30) Foreign Application Priority Data
Jun. 16, 2017 (DE) .................... 10 2017 113 259.7

(51) Int. Cl.
*A61N 2/02* (2006.01)
*A61N 1/40* (2006.01)

(52) U.S. Cl.
CPC ...... *A61N 2/02* (2013.01); *A61N 1/40* (2013.01)

(58) Field of Classification Search
CPC .... A61N 2/02; A61N 1/40; A61N 2005/0645; A61N 2005/0626; A61N 5/06; A61N 1/32
(Continued)

(56) References Cited

U.S. PATENT DOCUMENTS 5,458,142 A * 10/1995 Farmer .................... A61N 2/02
600/409
5,830,140 A * 11/1998 Dillinger ............ A61K 41/0004
600/407

(Continued)

FOREIGN PATENT DOCUMENTS

CN         100502977 C     6/2009
DE         29709094 U1    9/1998
(Continued)

OTHER PUBLICATIONS

Technote 4-Noise in Electronic Systems, Tim J. Sobering, May 1999 (Year: 1999).*
(Continued)

*Primary Examiner* — Sunita Reddy
(74) *Attorney, Agent, or Firm* — Carter, DeLuca & Farrell LLP

(57) ABSTRACT

The invention relates to a device for generating electrical, magnetic, and/or electromagnetic signals, which, at different treatment frequencies, can be used to treat the human body, an electronic noise element (22) being provided as a means for providing a noise signal, which noise signal can be used for the selection of a treatment frequency, the properties of which electronic noise element are at least partly dependent on at least one biophysical radiation emission of the human body.

8 Claims, 1 Drawing Sheet

Figure 1:
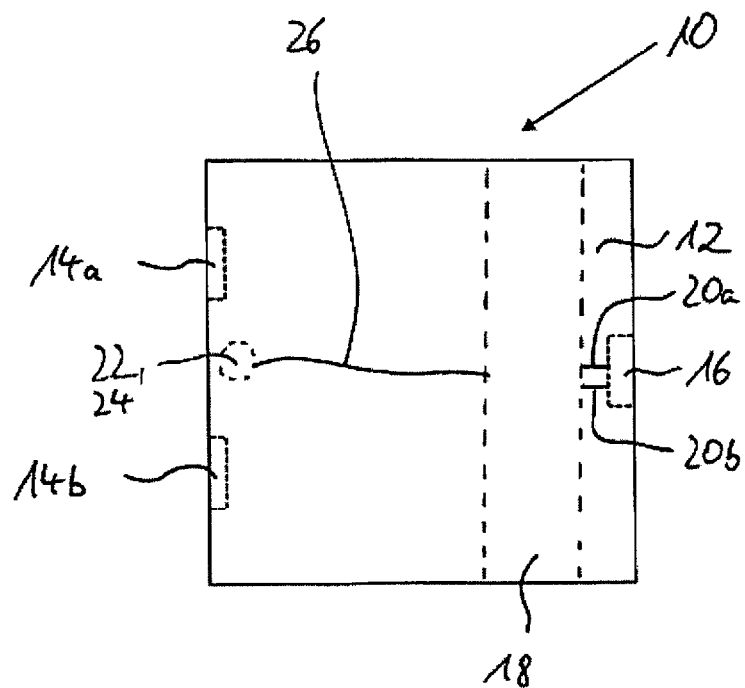

(58) Field of Classification Search
USPC .................................................... 600/9–15
See application file for complete search history.

(56) References Cited

U.S. PATENT DOCUMENTS

| | | | |
|---|---|---|---|
| 6,301,506 B1* | 10/2001 | den Boer | A61N 2/02 607/100 |
| 2002/0037026 A1* | 3/2002 | Sato | G01J 5/0225 374/132 |
| 2002/0099425 A1* | 7/2002 | Johnson | A61N 1/36021 607/67 |
| 2006/0064139 A1 | 3/2006 | Chung et al. | |
| 2006/0212077 A1 | 9/2006 | Pilla et al. | |
| 2008/0269847 A1* | 10/2008 | Nemenov | A61B 5/0059 607/89 |
| 2010/0082027 A1* | 4/2010 | Chalmers | A61N 1/36021 606/41 |
| 2011/0105916 A1* | 5/2011 | Rhodes | A61B 5/02405 600/485 |
| 2012/0143285 A1* | 6/2012 | Wang | A61B 5/4854 607/59 |
| 2012/0185016 A1* | 7/2012 | Weiner | A61N 5/00 607/62 |
| 2012/0253101 A1* | 10/2012 | Wang | A61N 2/004 600/9 |
| 2014/0197317 A1* | 7/2014 | Yang | G06F 1/3265 250/341.8 |
| 2015/0031964 A1* | 1/2015 | Bly | A61B 5/681 600/301 |
| 2015/0297888 A1* | 10/2015 | Rhodes | A61B 5/4035 607/62 |
| 2017/0136242 A1 | 5/2017 | Durand | |
| 2017/0293740 A1* | 10/2017 | Xing | A61B 10/0051 |
| 2017/0326331 A1* | 11/2017 | Joseph | A61B 5/486 |
| 2018/0043175 A1* | 2/2018 | Karpf | A61N 1/36021 |

FOREIGN PATENT DOCUMENTS

| | | |
|---|---|---|
| DE | 19752934 A1 | 12/1998 |
| DE | 10002251 A1 | 8/2001 |
| DE | 102015002565 A1 | 9/2016 |
| JP | 2000254239 A | 9/2000 |
| JP | 2013539690 A | 10/2013 |
| RU | 99124340 A | 9/2001 |
| RU | 2335308 C1 | 10/2008 |
| WO | 2005084753 A1 | 9/2005 |

OTHER PUBLICATIONS

EP Office Action for application No. 18 730 760.8 dated Feb. 2, 2021 with English translation.
International Search Report issued in PCT/EP2018/065337 dated Sep. 10, 2018, 3 pages.
International Preliminary Report on Patentability issued in corresponding PCT/EP2018/065337 dated Sep. 13, 2019, 9 pages.
German Office Action issued in corresponding German Application No. 10 2017 113 259.7 dated Apr. 20, 2020 with English Translation.
Search Report and Written Opinion for Singapore Application No. 11201912911S dated Apr. 22, 2021.
Office Action for Japanese Application No. 2020-519839 dated May 7, 2021.
Search Report issued in Russian Application No. 2020100729/14 dated Sep. 8, 2021 with English Translation.
Office Action issued in Russian Application No. 2020100729/14 dated Sep. 8, 2021.with English translation.
India Examination Report for application No. 202017000559 dated Feb. 23, 2022 with English Translation.
Columbia Office Action and Search Report for application No. PCT/EP2018/065337 dated Jan. 18, 2022. with English Translation.

* cited by examiner

DEVICE FOR GENERATING ELECTRICAL, MAGNETIC AND/OR ELECTROMAGNETIC SIGNALS FOR TREATING THE HUMAN BODY, AND METHOD FOR OPERATING SUCH A DEVICE

The invention relates to a device for generating electrical, magnetic and/or electromagnetic signals for treating the human body, and a method for operating a device for generating electrical, magnetic and/or electromagnetic signals for treating the human body.

From experience, devices for generating electrical, magnetic and/or electromagnetic signals for treating the human body are known, in particular in the form of electrostimulation devices. Such devices can be operated at different frequencies in most cases. The success of the application of the devices depends in many cases on the fact that a suitable treatment frequency is determined and applied for the respective individual case constellation. This often involves visiting a specialist with relevant experience and who, taking into account the circumstances of each individual case, determines and applies a suitable treatment frequency or recommends this for use. In particular, reference is made to the devices known from experience, which are marketed under the brand Timewaver in various implementations. Insofar, only by way of example reference is made in this respect to the products "Timewaver Frequency" and "Timewaver Home". The invention relates in particular to a further development of such products. All technical features of these products are hereby expressly referred to, in particular those features which are realized in all the products mentioned.

The invention is based on the object to provide a device for generating electrical, magnetic and/or electromagnetic signals for treating the human body and to provide a method for using such a device which presents a new and easy possibility to select a suitable treatment frequency.

According to the invention, the solution of the object is achieved with the features of the independent claims. Further practical embodiments are described in connection with the dependent claims.

In a device according to the invention for generating electrical, magnetic and/or electromagnetic signals which can be used with different treatment frequencies for treating the human body, as means for providing a noise signal which can be used for the selection of a treatment frequency, an electronic noise element is provided, the properties of which have an at least partial dependence on at least one biophysical radiation of the human body. By the term biophysical radiation is meant in particular all field, radiation and energy forms which can permanently surround or temporarily surround a human body, for example magnetic fields, electric fields, electromagnetic fields, infrared radiation, thermal radiation, acoustic radiation energy and/or mechanical energy. Any biophysical radiation comprising such fields, radiations and/or energies can—individually or in combination of several fields, radiations and/or energies—influence the properties of a noise element suitable for the invention.

Already at this point, reference is made in particular to radiation in the form of infrared radiation. Infrared radiation includes the spectral range with wavelengths between 1 mm and 780 nm, which corresponds to a frequency range of 300 GHz to 400 THz.

Particularly suitable for the invention are those electronic noise elements, the properties of which have a dependence in the spectral range in which the human body emits infrared radiation or other biophysical radiation, so that a device which is brought into the vicinity of the human body is influenced by this radiation of the human body.

Infrared radiation of the human body takes place in particular in the ranges of the near infrared (NIR) with wavelengths of 0.78 µm to 1.4 µm (IR-A) and 1.4 µm to 3.0 µm (IR-B) as well as in the range of medium infrared (MIR) with wavelengths of 3.0 µm to 50.0 µm. In this respect, particularly preferred are electronic noise elements which have a dependence on the corresponding infrared radiation, especially or exclusively in the abovementioned specific ranges. Explicit reference is furthermore made to the range with wavelengths of 10.0 µm±9.0 µm, that is, the range between 1.0 µm and 19.0 µm, more preferred in the range between 5.0 µm and 15 µm.

As an electronic noise element in the context of the invention is regarded as every electronic component, which outputs an output signal superimposed on the noise signal in addition to an output signal. In this regard, a distinction is made between active noise elements and passive noise elements within the scope of this disclosure.

As a passive noise element in the context of the invention are understood to be those electronic components which generate a measurable noise signal without an external energy supply such as a voltage source in the form of a power cable or a battery. In this regard, reference is made in particular to the p-n junction of infrared diodes, transistors or other components, which can generate a corresponding noise independently of the abovementioned power supplies. For the sake of completeness, reference is made to the fact that even passive noise elements can optionally be supplied with energy and in particular be applied with an auxiliary current. For devices according to the invention, such electronic noise elements are particularly suitable, which, upon application of an auxiliary current of less than 100 µA, generate a detectable increase in the noise range, in particular those noise elements which, with an auxiliary current of less than 50 µA or less than 30 µA, provide a corresponding increase of the frequency and/or the amplitude of the noise.

As active noise elements in the context of the invention, those elements are considered which, for generating a noise signal, inevitably have to be applied with external energy in the form of a supply voltage or a corresponding current, that is, an external energy storage. In this regard, reference is made to carbon film resistors by way of example.

A device according to the invention has the advantage that a noise signal which can be used to select a treatment frequency, can be influenced individually, in particular due to biophysical radiation of a body of a person to be treated, such as, e.g., infrared radiation, so that, by interaction between a human body of a person to be treated and a resulting noise influenced by the corresponding radiation of the human body (e.g., infrared radiation), a suitable selection of a treatment frequency may take place.

In particular, the invention relates to compact devices (so-called wearables) that can be positioned and operated in the immediate vicinity of the body, which can be carried along on the body and be operated by portable energy storage.

The following features of a device according to the invention are realized—both individually and in any combination with each other—in advantageous embodiments:

a) A device according to the invention preferably has a connection for a portable energy storage in the form of a battery. The energy storage can be permanently installed and/or removed for replacing or charging.

b) The device preferably has a size of less than 20 cm×10 cm×5 cm, preferably a size of less than 10 cm×10 cm×3 cm, and particularly preferred, a size of less than 8 cm×8 cm×2 cm.

c) The device preferably has connections for at least two poles (+/−) for connecting electrodes in order to be able to introduce electrical signals into a human body via such electrodes. As suitable electrodes, reference is made in particular to ear clips, adhesive electrodes and hand electrodes.

d) The device preferably has connections for at least two poles (+/−) for connecting of equipment for the emission of electromagnetic signals. In this regard, reference is made in particular to the possibility of connecting magnetic field coils.

e) The device preferably has a connection for charging a portable energy storage, in particular a connection in the form of a USB socket or in the form of another screw and/or plug connector.

f) The device is preferably designed to be operated at treatment currents of 0 μA to 4000 μA. Particularly preferred, the device is designed to be operated with treatment currents from 0 μA to 1000 μA. In this context, the term treatment currents is used to denote the currents that can be introduced into a human body to be treated by a device according to the invention, that is, the currents emitted by the device.

g) The device is preferably designed to be operated at treatment frequencies between 0 Hz and 1 MHz.

h) The device is preferably designed to be able to deliver treatment voltages between 0 V and 24 V, in particular treatment voltages between 0 V and 12 V and particularly preferred between 0 V and 10 V.

In a practical embodiment of a device according to the invention, the means for providing a noise signal that can be used for selecting a treatment frequency is a sensor for detecting an electric, magnetic or electromagnetic field, a sensor for detecting infrared radiation or a sensor for detecting heat radiation. Two, three or more such sensors may naturally also be provided. With all the sensors mentioned above, a noise signal can be generated for a device according to the invention. This noise signal can be used as a basis for the inventive method still to be described below. It is thereby advantageous that at least a biophysical radiation of human, in particular a person to be treated, can influence the noise signal when the device with the sensor element is brought into the vicinity of the human body. Thus, the treated person himself can be considered at least partially as a control or regulation element of such a device, whereby a novel, individual determination of treatment frequencies is made possible, which takes account of the biophysical radiation of the person to be treated.

With a suitable optional program, which will be discussed in more detail in the following, reactions of the human body to an immediately preceding treatment with a device according to the invention can be taken into account, so that a control method for selecting the treatment frequency can be carried out while taking into account the biophysical radiation.

As sensors for magnetic fields, reference is made in particular to Hall sensors and Wiegand sensors.

In particular, capacitive sensors can be used as sensors for the detection and consideration of electric fields.

As sensors for electromagnetic fields, reference is made in particular to magneto-inductive sensors.

For the detection and consideration of infrared radiation, reference is made in particular to infrared photodiodes and to pyrometers.

And to record heat radiation (MIR), reference is made to germanium photodiodes and silicon photodiodes.

For the sake of completeness, it is also pointed out again that acoustic energy (structure-borne noise) can be detected and taken into account, in particular with the aid of a noise element in the form of a piezoelectric sensor.

The same applies to mechanical energy, which can be detected and taken into account, for example, via semiconductor-based strain gauges.

If a passive noise element is provided, this has the advantage that a corresponding noise signal is available even without an external power supply in a particularly efficient and cost-effective manner. Particularly suitable are passive noise elements, which can optionally also be operated as active noise elements, in particular by being applied with an auxiliary current as explained above, if necessary. The application of a corresponding auxiliary current can be advantageous insofar as the realization of a corresponding device, in particular if the noise signal is to be digitized for the intended selection, first has to be prepared in order to make an appropriate selection of the treatment frequency in a suitable manner.

In particular, reference is made in this context to the possibility of using, as a means for providing a noise signal that can be used for selecting a treatment frequency, a sensor for detecting infrared radiation in the form of an infrared diode or to provide such an infrared diode in a corresponding device, the p-n junction of which serves as a passive noise element. Such infrared diodes are not only relatively inexpensive as electronic components, as they are produced in large quantities in particular also for other applications, but they also have the advantage that the service life of such infrared diodes is very high, in particular higher than the expected service life or useful life of a device according to the invention. Insofar it can be assumed to be highly likely that, through the use of such an infrared diode, that the device according to the invention will function safely with respect to the noise signal over a long period of time.

In a further practical embodiment of a device according to the invention, a noise voltage is provided as noise signal. This means that the so-called noise is monitored as an output signal of the noise element and is used as a noise signal of the device according to the invention for the selection of a suitable treatment frequency. The use of a noise voltage as a noise signal represents an economically viable alternative to the use of a noise current insofar as the processing of a signal in the form of a noise voltage is technically simpler and thus more cost-effective. For this, a high-frequency operational amplifier can be used for in particular.

Basically, the evaluation of the noise signal is possible in any manner. In practice, it has proven to be particularly suitable to use means for signal processing for evaluating the noise signal and to generate a digital data stream of the noise signal. In this regard, particular attention is paid to means for generating a very simple digital data stream in the form of a 1-bit data sequence consisting exclusively of results in the form of a 0 or a 1.

In this context, particular reference is made to the possibility of attenuating the useful spectrum of the electronic noise element, in particular by using the means for signal processing and for generating a digital data stream, and to amplify the noise spectrum. Thus, a higher resolution of the noise can be generated.

In a further practical embodiment of a device according to the invention, means for the statistical evaluation of the digital data stream and means for determining a treatment frequency dependent on the statistical evaluation are provided for evaluating the noise signal. In this context, it has to be taken into account that the statistical evaluation, due to the at least partial dependence of the noise elimination on infrared radiation, depends on the arrangement of a device according to the invention relative to a human body emitting infrared radiation. In other words, the selection of the treatment frequency is directly dependent on the positioning of a device according to the invention in the vicinity of a human body, in particular when the device is positioned so close to a human body that the infrared radiation emanating from the human body directly reaches the electronic noise element and thus affects its properties.

The invention also relates to a method for using a device as described above. According to the method, the device is brought close to the body of a human body to be treated prior to and/or during use of the device such that the biophysical radiation of the human body interacts with the electronic noise element, so that the selection of the treatment frequency takes place in dependence on the biophysical radiation of the human body to be treated. With regard to the advantages of the method according to the invention, reference is made to the advantages already described above in connection with the device according to the invention. Also in this regard, explicit reference is again made to the biophysical radiation in the form of infrared radiation of the human body.

In a practical embodiment of a method according to the invention, the distance of the device to the body to be treated prior to and/or during the application is maximally 50 cm. It is assumed that most of the biophysical radiations of a human body, in particular infrared radiation, will still have an influence on a suitable noise element in an inventive device at such a distance. However, since the intensity of the biophysical radiation, in particular of the infrared radiation, is greater with decreasing distance, it is preferred if the distance between the device and the body to be treated is at most 25 cm, more preferably maximally 10 cm and particularly preferred maximally 5 cm. Accordingly, the device according to the method of the invention is preferably worn directly on the body of a person to be treated, so that the distance between the noise element and the human body to be treated is minimized.

In a further practical embodiment of the method according to the invention, the electronic noise element is subjected to an auxiliary current. In this regard, once again, reference is again made to the preferred use of a passive noise element in the form of an infrared diode or a transistor with a corresponding p-n junction. The application of such an electronic noise element with an auxiliary current has the advantage that a preparation and digitization of the signal, as described above, for generating a short-term and simple selection decision regarding the treatment frequency can be realized easily and inexpensively.

A method according to the invention can be carried out in such a way that prior to or at the start of the treatment of a human body, a suitable treatment frequency is first determined as described above and then adjusted by the device according to the invention. In this case, the treatment can be carried out over a predetermined period of time with the determined treatment frequency.

In another variant of the method according to the invention, after expiry of a certain period of time, a new treatment frequency can also be determined and adjusted by the device. The device according to the invention can have a corresponding control for this purpose, which comprises a corresponding operating program which supports a user of a device according to the invention in the implementation of a corresponding method.

In this respect, a method according to the invention can also be carried out in such a way that, after a preset period of, for example, 10 seconds, 20 seconds, 30 seconds or any other duration value which is fixed, a new treatment frequency can determined and adjusted by the device, so that, in each case for a predetermined period of time, the treatment of the human body takes place with the respectively determined treatment frequency. For this, in a device according to the invention, a corresponding program or several programs can be firmly stored and/or the device can be configured in a programmable manner such that the user of the device himself can configure and store individual programs.

In particular, in conjunction with the programs mentioned above, a device according to the invention can be suitable for enabling a regulation of the treatment frequency to the extent that the infrared radiation of the human body represents a regulation parameter for the treatment frequency. Thereby, the infrared radiation of the human body is a regulation parameter (in contrast to a control parameter) in this respect, as it is to be assumed that there is an interaction between both the treatment frequency and the human body (including its infrared radiation) and an interaction between the human body (including the infrared radiation) and the treatment frequency. In particular—while considering the initial infrared radiation of the human body to be treated—the determined treatment frequency can lead to the fact that the infrared radiation of the human body—due to the effect of the electrical, magnetic and/or electromagnetic signals in the selected treatment frequency—changes during the period of the first treatment phase and this change in turn leads to a further change in the next treatment frequency. Depending on the individual case, this can lead to a change in the treatment frequency after each period of time or to the fact that the treatment frequency "settles" at a certain frequency value, successively approaching a certain target frequency value or even assumes a completely different value after each time period.

It is important that the biophysical radiation of the human body of the treating person, in particular the infrared radiation, can regulate or control the selection of the treatment frequency.

One can in particular speak of a control of the treatment frequency in those cases, in which initially, again taking into account the biophysical radiation of the human body of the treating person, a treatment frequency is determined and the device is then maintained for a certain treatment phase so that there is no feedback of any possibly changing biophysical radiation, especially infrared radiation, of the human body during the treatment.

For the sake of completeness, it is pointed out that the treatment frequency can also be determined and varied by means of other programs during the treatment or respectively before a treatment. In this regard, reference is made in particular to the possibility of re-determining the treatment frequencies after a non-predefined period of time, for example a new regular or irregular potential frequency can be determined for this and this new treatment frequency can only be adjusted if certain events occur, for example, when the new potential treatment frequency deviates by more than 10 percent from the old treatment frequency.

Figure 2:
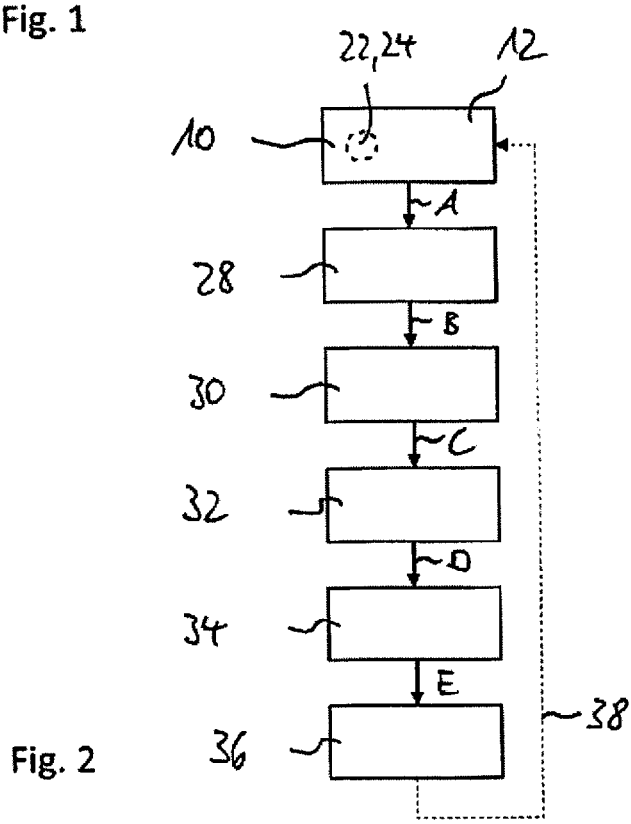

Further practical embodiments and advantages of the invention are described in the following in conjunction with the drawings. They show in:

FIG. 1 a schematic representation of a device according to the invention; and FIG. 2 a schematic representation of the operating principle of the device according to the invention shown in FIG. 1 during use.

FIG. 1 shows a schematic representation of a device 10 according to the invention. The device comprises a relatively small housing 12 in its geometric dimensions, so that it can be worn comfortably on the body of a person—and if desired also hidden. In the exemplary embodiment shown, the outer dimensions of the housing 12 are 5 cm (length)×5 cm (width)×1 cm (depth).

The weight of the represented device is less than 1 kg, in particular less than 800 g and preferably less than 500 g. Due to its size and weight, it can be carried along by a person—even over longer periods of time—without it being perceived as a heavy weight load. It is thus a so-called "wearable".

On the housing 12, a first connection 14*a* for a positive pole and a second connection 14*b* for a negative pole are provided. By way of these connections 14*a*, 14*b*, electrodes (not shown), magnetic coils or other additional devices that may be suitable for contact or non-contact introduction of electrical, magnetic and/or electromagnetic signals on a human body of a person to be treated can be optionally connected.

On the housing 12, a power and data connection 16 is further provided for charging an energy storage 18 shown only schematically, which is arranged inside the housing 12 in a protected manner and which is connected to the power and data connection 16 via electrical lines 20*a*, 20*b*. The energy storage 18 is a rechargeable battery in this exemplary embodiment, the power and data connection 16 is a USB port.

Further, in the housing 12 is arranged an electronic noise element 22 in the form of an infrared diode 24, here near an outer side of the housing 12, as means for providing a noise signal that can be used for selecting a treatment frequency. This infrared diode 24 can be applied with an auxiliary current via a line 26 from the energy storage 18 A—not shown in FIG. 1—passage area in the form of a recess and/or a housing portion permeable to infrared radiation, for example in the form of an infrared window is located in the housing 12.

The device 10 comprises further, not shown in detail, elements, in particular an on/off switch and optional operating buttons. Alternatively, the device 10 can also have a radio transmitter, which is connected to a control, not shown, and which makes it possible to wirelessly connect and control the device with a mobile terminal device, in particular via a mobile telephone (preferably a smartphone), a tablet PC or another mobile terminal device.

FIG. 2 shows the operating principle of a device 10 according to the invention in a schematic representation during use. The device 10 is represented in FIG. 2 in a highly abstracted manner only with the noise element 22 arranged in the housing 12, which in the exemplary embodiment is in the form of an infrared diode 24. The remaining elements, as, e.g., an energy storage etc. are also present but not represented in FIG. 2.

When the device 10 is brought into the proximity of a person, not represented, in particular a person to be treated with the device 10, the infrared radiation of that person acts directly on the noise element 22 and changes the properties of the noise. However, a prerequisite for this is that the distance between the device 10 and the person is sufficiently small, in particular no more than 20 cm, preferably no more than 10 cm and more preferably no more than 5 cm.

The noise of the noise element 22 influenced by the infrared radiation is now optionally amplified in a first step A by means of an amplifier 28. In particular, a known operational amplifier can serve this purpose.

By means of a further optional step B, the noise is then supplied to an AC/DC converter 30 in an optional step C and finally supplied to a filter 32 in a further optional step D.

This is followed by a further processing of the noise in a step E by means of a digitizing device, in particular in the form of a comparator 34, in order to generate a digitized noise signal in the form of a bit stream, before a selection of a treatment frequency takes place by means of a statistical evaluation unit 36 in a last optional step E.

The dashed arrow 38 indicates that the treatment frequency, when applied to the body, not represented, of the person to be treated, can in turn have a feedback to a treatment frequency to be newly determined, possibly with the device 10.

The features of the invention disclosed in the present description, in the drawings and in the claims may be essential both individually and in any desired combinations for the realization of the invention in its various embodiments. The invention is not limited to the described embodiments. It can be varied within the scope of the claims and taking into account the knowledge of the competent person skilled in the art.

LIST OF REFERENCE NUMERALS

10 Device
12 Housing
14*a*, 14*b* Connection
16 Current and data terminal (USB)
18 Energy store (battery)
20*a*, 20*b* Line
22 Noise element
24 Infrared diode
26 Line
28 Amplifier
30 AC/DC transducer
32 Filter
34 Comparator
36 Evaluation unit
38 Arrow

The invention claimed is:

1. A device for generating electrical, magnetic and/or electromagnetic signals for use with different treatment frequencies configured to treat a human body, the device comprising:

an electronic noise element as means of providing a first signal that is used for a selection of a treatment frequency of the different treatment frequencies, wherein the first signal deliberately includes electronic noise, wherein properties of the treatment frequency have at least a partial dependence on at least one infrared radiation of the human body having a wavelength between 0.78 um and 3.0 um, wherein the electronic noise element outputs an output signal superimposed on the first signal in addition to the output signal and wherein the first signal is individually influenced by the infrared radiation of the human body to be treated, wherein by interaction between the human body to be treated and a resulting signal influenced by a corresponding radiation of the human body, a selection of the treatment frequency takes place, wherein the device is configured for signal processing and for generating a digital data stream of the first signal for evaluating the first signal, and wherein the device is configured for a statistical evaluation of the digital data stream and for determining the treatment frequency dependent on the statistical evaluation for evaluating the first signal, and wherein the electronic noise element includes at least a sensor for detecting infrared radiation in the form of an infrared diode including a p-n junction serving as a passive noise element.

2. The device of claim 1, wherein the electronic noise element further includes at least one sensor for detecting an electrical, magnetic or electromagnetic field, or a sensor for detecting heat radiation.

3. The device of claim 1, wherein a voltage is provided as the first signal.

4. A device for generating electrical, magnetic and/or electromagnetic signals for use with different treatment frequencies configured to treat a human body, the device comprising:
an electronic noise element that provides a first signal used for a selection of a treatment frequency of the different treatment frequencies, wherein the first signal intentionally includes electronic noise, wherein properties of the treatment frequency have at least a partial dependence on at least one infrared radiation of the human body having a wavelength less than 3.0 um, wherein the electronic noise element outputs an output signal superimposed on the first signal in addition to the output signal, wherein the first signal is configured to be influenced by the infrared radiation of the human body to be treated, wherein by interaction between the human body and a resulting signal influenced by a corresponding radiation of the human body, the electronic noise element selects the treatment frequency, wherein the device is configured to process signals and generate a digital data stream of the first signal for evaluating the first signal, and wherein the device is configured to provide a statistical evaluation of the digital data stream and determine the treatment frequency dependent on the statistical evaluation based on the first signal, and
wherein the electronic noise element includes at least a sensor for detecting infrared radiation in the form of an infrared diode including a p-n junction serving as a passive noise element.

5. The device of claim 4, wherein the electronic noise element further includes at least one sensor for detecting an electrical, magnetic or electromagnetic field, or a sensor for detecting heat radiation.

6. The device of claim 4, wherein a voltage is provided as the first signal.

7. A device for generating electrical, magnetic and/or electromagnetic signals for use with different treatment frequencies configured to treat a human body, the device comprising:
an electronic noise element that generates an output noise signal which intentionally includes electronic noise, the output noise signal being used for a selection of a treatment frequency of the different treatment frequencies, wherein properties of the electronic noise element have at least a partial dependence on at least one biophysical radiation of the human body having a wavelength between 0.78 um and 3.0 um, wherein the electronic noise element outputs an output signal superimposed on the output noise signal in addition to the output signal and wherein the output noise signal is individually influenced by the biophysical radiation of the human body to be treated, wherein by interaction between the human body to be treated and a resulting signal influenced by a corresponding radiation of the human body, a selection of the treatment frequency takes place,
wherein the device is further configured for signal processing and for generating a digital data stream of the output noise signal for evaluating the output noise signal,
wherein the device is further configured for a statistical evaluation of the digital data stream and for determining the treatment frequency dependent on the statistical evaluation for evaluating the output noise signal,
wherein the electronic noise element includes at least a sensor for detecting infrared radiation in the form of an infrared diode including a p-n junction which serves as a passive noise element, and
wherein a voltage is provided as the output signal.

8. The device of claim 7, wherein the electronic noise element further includes at least one sensor for detecting an electrical, magnetic or electromagnetic field, a sensor for detecting biophysical radiation, or a sensor for detecting heat radiation.

* * * * *

UNITED STATES PATENT AND TRADEMARK OFFICE
CERTIFICATE OF CORRECTION

PATENT NO. : 11,517,759 B2
APPLICATION NO. : 16/623156
DATED : December 6, 2022
INVENTOR(S) : Marcus Schmieke, Andreas Hilburg and Matthias Krzizan It is certified that error appears in the above-identified patent and that said Letters Patent is hereby corrected as shown below:

In the Claims

In Claim 1, Column 8, Line 61, delete the phrase "0.78 um and 3.0 um" and insert --0.78 µm and 3.0 µm--
In Claim 4, Column 9, Line 28, delete the phrase "3.0 um" and insert --3.0 µm--
In Claim 7, Column 10, Line 18, delete the phrase "0.78 um and 3.0 um" and insert --0.78 µm and 3.0 µm--

Signed and Sealed this
Thirtieth Day of January, 2024

Katherine Kelly Vidal
*Director of the United States Patent and Trademark Office*